United States Patent [19]

Leonard et al.

[11] Patent Number: 5,011,830

[45] Date of Patent: Apr. 30, 1991

[54] ORAL COMPOSITIONS HAVING IMPROVED ANTICALCULUS PROPERTIES CONTAINING PYROPHOSPHATE AND AN ACRYLIC ACID POLYMER

[75] Inventors: Giles J. Leonard, Oxford; Michael L. Marberry, Cincinnati, both of Ohio

[73] Assignee: The Proctor & Gamble Company, Cincinnati, Ohio

[21] Appl. No.: 554,936

[22] Filed: Jul. 16, 1990

Related U.S. Application Data

[63] Continuation of Ser. No. 375,211, Jul. 3, 1989, abandoned, which is a continuation of Ser. No. 129,268, Dec. 7, 1987, abandoned.

[51] Int. Cl.$^5$ .......................... A61K 7/18; A61K 7/16
[52] U.S. Cl. .......................................... 424/57; 424/49; 424/52; 424/58; 514/901
[58] Field of Search ...................... 424/49, 52, 57, 58; 514/901

[56] References Cited

U.S. PATENT DOCUMENTS

| | | | |
|---|---|---|---|
| 3,429,963 | 2/1969 | Shedlovsky | 424/56 |
| 4,138,477 | 2/1979 | Gaffar | 424/52 |
| 4,152,420 | 5/1979 | Gaffar et al. | 424/52 |
| 4,515,772 | 5/1985 | Parran et al. | 424/57 |
| 4,627,977 | 12/1986 | Gaffar et al. | 424/52 |
| 4,661,341 | 4/1987 | Benedict et al. | 424/48 |

FOREIGN PATENT DOCUMENTS 1222197 2/1971 United Kingdom .

*Primary Examiner*—F. T. Moezie
*Attorney, Agent, or Firm*—Douglas C. Mohl; Jack D. Schaeffer; Richard C. Witte

[57] ABSTRACT

The present invention relates to oral hygiene compositions having improved anticalculus activity containing a mixture of a sodium and potassium pyrophosphate salt and a polyacrylic acid or salt thereof or copolymers of acrylic acid and another monomer or mixtures thereof and an effective amount of a water soluble fluoride salt in a pharmaceutically acceptable carrier to provide enhanced anticalculus benefits.

13 Claims, No Drawings

ORAL COMPOSITIONS HAVING IMPROVED ANTICALCULUS PROPERTIES CONTAINING PYROPHOSPHATE AND AN ACRYLIC ACID POLYMER

This is a continuation of application Ser. No. 375,211, filed on July 3, 1989, which is a continuation of Ser. No. 129,268, filed on Dec. 7, 1987, both are abandoned.

TECHNICAL FIELD

The present invention relates to oral compositions containing a mixture of a pyrophosphate salt and a polyacrylic acid, which provide unexpected anticalculus benefits.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Patent No. 490,384, Feb. 15, 1937, discloses oral compositions containing ethylenediaminetetraacetic acid, nitrilotriacetic acid and related compounds as anticalculus agents. U.S. Pat. No. 3,678,154, July 18, 1972 to Widder et al. discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been included for a variety of purposes, some for providing an anticalculus benefit. Included among such references are U.S. Pat. No. 2,941,926, June 21, 1960 to Salzmann et al. which discloses dental powders containing chlorophyll and pyrophosphate salts. U.S. Pat. No. 3,137,632, June 16, 1964 to Schiraldi discloses toothpastes containing pyrophosphate salts. U.S. Pat. Nos. 3,927,201 and 202, Dec. 16, 1975 to Baines et al. and Harvey et al., respectively, disclose toothpastes which utilize soluble pyrophosphates as abrasives. U.S. Pat. Nos. 4,244,931, Jan. 13, 1981 and 4,247,526, Jan. 27, 1981 to Jarvis et al. disclose pyrophosphate salts in dicalcium phosphate systems. Jap. Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions. U.S. Pat. No. 4,515,772, May 7, 1985 to Parran, et al., discloses compositions containing soluble pyrophosphate salts as anticalculus agents. Parran et al. achieve soluble pyrophosphate systems through the use of acid pyrophosphate salts.

In addition to the use of the above mentioned materials the use of certain acrylic acid polymers and other agents have also been disclosed for use as anticalculus agents. Included among such agents are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Another reference disclosing polyacrylic acids in oral compositions is South African Patent No. 720,898, Sept. 12, 1972 which discloses such acids having a molecular weight in the range of 2,000 to 4,000,000 for use as a membrane to prevent the elution from teeth of previously applied agents. U.S. Pat. No. 3,956,480, May 11, 1976 to Gaffar discloses complexes of anionic polymers (e.g. acrylic acid) and a cationic therapeutic agent (e.g., chlorhexidine) as anticalculus agents. Strontium chelates have also been disclosed for use in oral compositions, particularly in the enhancement of fluoride uptake.

The effect of a strontium-EDTA complex in combination with sodium ricinoleate and a fluoride source is found in the Journal of Dental Research (1982) 61 (3) 451-455. The combined effect of strontium and fluoride in reducing the acid solubility of enamel is also disclosed in the Journal of Dental Research (1983) 62 (10) 1049-1053. A further reference discussing the effect of strontium and fluoride is Featherstone, J.D.B. "Remineralization of Artificial Carious Lesions In-vivo and In-vitro", Proceedings Workshop (1983) IRL Press Ltd.

The use of strontium in combination with fluoride in oral compositions is also disclosed in a number of patent references. Included among these references are U.S. Pat. No. 3,888,976, June 10, 1975 to Mlkvys disclosing an effervescent mouthwash tablet containing strontium ions and possibly a fluoride ion source. U.S. Pat. No. 4,367,219, Jan. 4, 1983 to Schole discloses dentifrices containing a combination of strontium EDTA, a ricinoleate salt and a fluoride ion source. U.S. Pat. No. 4,425,549, Nov. 15, 1983 to Shah et al. discloses toothpastes containing a glycyrrhizinate salt, strontium EDTA and a fluoride ion source. Finally European Patent Application No. 0,079,611, June 6, 1983, Shah, discloses oral compositions containing a strontium EDTA complex and a fluoride ion source.

Although there have been a number of approaches disclosed for combatting caculus, there is still the desire and need to develop improved products possessing that property. The prior art while disclosing the use of pyrophosphate salts and polyacrylic acid provides no suggestion to use such materials in a mixture wherein the materials are present in amounts sufficient to achieve the desired level of anticalculus efficacy.

It is an object of the present invention to provide compositions which delivers an anticalculus benefit.

It is a further object of the present invention to produce an effective anticalculus product using a mixture of a pyrophosphate salt and a polyacrylic acid which delivers improved anticalculus performance.

It is still a further object of the present invention to provide anticalculus products which are cosmetically acceptable and do not inhibit remineralization of the teeth.

It is still a further object of the present invention to provide effective methods for combating calculus using the compositions described herein.

These and other objects will become more clear from the detailed description which follows.

All percentages and ratios used herein are by weight unless otherwise specified. Also all measurements referred to herein are made at 25° C. in the composition or on the pure material unless otherwise specified.

SUMMARY OF THE INVENTION

The present invention embraces an oral composition comprising:
(a) a safe and effective amount of a pyrophosphate salt or a mixture of said salts;
(b) a safe and effective amount of a polyacrylic acid or mixture thereof;
(c) a safe and effective amount of a soluble fluoride ion source; and
(d) a pharmaceutically acceptable carrier.

The present invention also encompasses a method for retarding development of dental calculus using the compositions described herein.

DETAILED DESCRIPTION OF THE INVENTION

The compositions of the present invention comprise a mixture of a pyrophosphate salt(s) and a polyacrylic acid(s) in a pharmaceutically acceptable carrier.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "pharmaceutically acceptable carrier", as used herein, is meant a suitable carrier which can be used to apply the present anticalculus agents in the oral cavity without undue toxicity irritation allergic response and the like, commensurate with a reasonable benefit/risk ratio.

Pyrophosphate Salts

The pyrophosphate salts used in the present compositions can be any of the alkali metal (including ammonium) pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. The amount of pyrophosphate salt useful in the present composition is any effective amount and is generally enough to provide at least 1.0% $P_2O_7^{-4}$, preferably from about 1.5% to about 6%, more preferably from about 3.0% to about 6%, to the compositions. It is to be appreciated that the level of $P_2O_7^{-4}$ is that capable of being provided to the composition (i.e., the theoretical amount at an appropriate pH) and that other pyrophosphate forms (e.g., $HP_2O_7^{-3}$) may be present when a final product pH is established. Mixtures of the salts can be used to provide the pyrophosphate species.

Pyrophosphate salts are described in more detail in Kirk & Othmer, *Encyclopedia of Chemical Technology*, Second Edition, Volume 15, Interscience Publishers (1968), incorporated herein by reference.

Polyacrylic Acid

The second anticalculus agent useful in the compositions of the present invention includes polyacrylic acid polymers or copolymers having a mass average molecular weight of from about 1,000 to about 40,000.

Polyacrylic acid polymers are staple items of commerce and are made by polymerizing acrylic acid

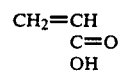

to form the repeating chain

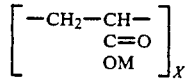

the repetition, X, being sufficient to provide the molecular weight desired. M may be an alkali metal or ammonium ion or hydrogen. Polymers of the type useful in the present invention are available from Rohm and Haas Company.

Copolymers of acrylic acid and other monomers may also be used in the present invention. Suitable other monomers include methacrylic acid, 2-hydroxypropyl acrylate, 3-hydroxypropyl methacrylate, 3-hydroxy propyl acrylate and acrylamide. It is preferred that with methacrylic acid, the number of acrylic acid units in the polymer be at least 50% of the total units present. With other monomers it is preferred that the percentage be at least 80%. Mixtures of other monomers may also be used.

While the molecular weight may be in the range of about 1,000 to about 40,000, preferably the molecular weight is from about 2,000 to about 8,000, most preferably from about 3,500 to about 7,500. A particularly preferred material is a polyacrylic acid polymer having a molecular weight of about 4500 which can be provided by Rohm and Haas carrying the identification LMW-45N.

The amount of the polymer used in the present compositions is generally from about 0.1% to about 10%, preferably from about 0.1% to about 5.0%, most preferably from about 0.1% to about 4%. Mixtures of polyacrylic acid polymers or copolymers are also useful in the present invention.

Water Soluble Fluoride Ion Source

Water-soluble fluoride compounds in the present compositions are present in an amount sufficient to give a fluoride concentration of from about 0.0025% to about 5.0% by weight, preferably from about 0.005% to about 2.0% by weight, to provide pyrophosphate ion stability as well as anticaries efficacy. Preferred fluorides are sodium fluoride, stannous fluoride, indium fluoride, and sodium monofluorophosphate. Norris et al., U.S. Pat. No. 2,946,735, issued July 26, 1960 and Widder et al., U.S. Pat. No. 3,678,154, issued July 18, 1972 disclose such salts as well as others. Both patents are incorporated herein by reference.

Pharmaceutically Acceptable Carrier

The carrier for the polyacrylic acid polymer or copolymer and pyrophosphate salt(s) can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and pyrophosphates. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, July 29, 1982, incorporated herein by reference.

The abrasive in the compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to dentifrice compositions. Suitable flavoring gents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including nonsoap anionic, nonionic, cationic, zwitterionic and amphoteric organic synthetic detergents. Many of these suitable surfactants are disclosed by Gieske et al. in U.S. Pat. No. 4,051,234, Sept. 27, 1977, incorporated herein by reference.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can comprise the carrier for the anticalculus agents of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH which is safe for the mouth's hard and soft tissues. Such pH's are generally from about 3 to about 10, preferably from about 4 to about 8.5.

METHOD OF MANUFACTURE

The carrier compositions of the present invention can be made using methods which are common in the oral products area.

For example, toothpaste compositions may be prepared by mixing part of the humectant and water together and heating to 66°–71° C. The fluoride source, if present, is then added along with the sweetener, the polyacrylic acid polymer or copolymer and the pyrophosphate salt(s), the opacifier and the flavor. To this mixture is added the abrasive which is mixed in well. The thickener is then slurried with the remainder of the humectant and milled prior to being added to the other components.

COMPOSITIONS USE

The present invention in its method aspect involves applying to the oral cavity safe and effective amounts of the anticalculus agents. Generally an amount of at least about 0.025 grams of the polymer and at least about 0.150 grams of the pyrophosphate salt(s).

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES I–IV

The following are compositions representative of the present invention.

| Component | Weight % | | | |
|---|---|---|---|---|
| | I | II | III | IV |
| Sorbitol (70% Aqueous Solution) | 35.000 | 35.000 | 35.000 | 35.000 |
| Distilled Water | 14.298 | 13.563 | 11.713 | 10.483 |
| Sodium Fluoride | 0.243 | 0.243 | 0.243 | 0.243 |
| Glycerin | 5.000 | 5.000 | 5.000 | 5.000 |
| Ioto Carrageenan | 0.750 | 0.750 | 0.750 | 0.750 |
| Sodium Saccharin | 0.280 | 0.280 | 0.280 | 0.280 |
| Tetrasodium Pyrophosphate | 1.635 | 2.200 | 3.400 | 2.600 |
| Sodium Acid Pyrophosphate | 0.550 | 0.720 | 1.370 | — |
| Tetrapotassium Pyrophosphate | — | — | — | 3.400 |
| Polyacrylic Acid (LMW-45N)[1] | 14.700 | 14.70 | 14.700 | 14.700 |
| Titanium Dioxide | 0.500 | 0.50 | 0.500 | 0.500 |
| Flavor | 1.044 | 1.044 | 1.044 | 1.044 |
| Precipitated Silica | 20.000 | 20.000 | 20.000 | 20.000 |
| Sodium Alkyl Sulfate (27.4% Aqueous Solution) | 4.000 | 4.000 | 4.000 | 4.000 |
| Sylox 15 | 2.000 | 2.000 | 2.000 | 2.000 |
| | 100.000% | 100.000% | 100.000% | 100.000% |

[1]Offered by Rohm and Haas as LM-45N having mass average molecular weight of 4500. A solution of 45.6% solids is used.

What is claimed is:

1. An anticalculus oral composition comprising:
   (a) a safe and effective amount of a pyrophosphate salt or a mixture of said salts;
   (b) a safe and effective amount of polyacrylic acid or copolymers of acrylic acid and another monomer or mixtures thereof;
   (c) a safe and effective amount of a water soluble fluoride ion source; and
   (d) a pharmaceutically acceptable carrier.

2. An anticalculus composition according to claim 1 wherein the pyrophosphate salt is selected from the group consisting of sodium acid pyrophosphate, tetrapotasium pyrophosphate, tetrapotassium pyrophosphate.

3. An anticalculus composition according to claim 2 wherein the fluoride ion source is selected from the group consisting of sodium fluoride, stannous fluoride.

4. An anticalculus composition according to claim 3 wherein polyacrylic acid is present.

5. An anticalculus composition according to claim 4 which is in the form of a toothpaste containing a dental abrasive.

6. An anticalculus composition according to claim 5 wherein the fluoride ion source is sodium fluoride.

7. An anticalculus composition according to claim 6 wherein the dental abrasive is a silica dental abrasive.

8. An anticalculus composition according to claim 4 which is in the form of a mouthrinse containing a humectant and ethanol.

9. An anticalculus composition according to claim 8 wherein the fluoride ion source is sodium fluoride.

10. A method of reducing calculus by applying to dental enamel a safe and effective amount of a composition according to claim 1.

11. A method according to claim 10 wherein the polymer is polyacrylic acid.

12. A method according to claim 10 wherein the composition is in the form of a toothpaste and contains a silica dental abrasive.

13. A method according to claim 10 wherein the composition is in the form of a mouthrinse containing a humectant and ethanol.

* * * * *